(12) United States Patent
Kreidler

(10) Patent No.: US 7,452,361 B2
(45) Date of Patent: Nov. 18, 2008

(54) SYSTEM WITH A SCREWDRIVER AND A BONE SCREW

(75) Inventor: Winfried Kreidler, Tuttlingen (DE)

(73) Assignee: Richard Martin Medizintechnik GmbH, Tuttlingen (DE)

( * ) Notice: Subject to any disclaimer, the term of this patent is extended or adjusted under 35 U.S.C. 154(b) by 341 days.

(21) Appl. No.: 11/091,658

(22) Filed: Mar. 28, 2005

(65) Prior Publication Data

US 2005/0216015 A1 Sep. 29, 2005

(30) Foreign Application Priority Data

Mar. 27, 2004 (DE) .................. 20 2004 004 844 U

(51) Int. Cl.
*A61B 17/58* (2006.01)
*A61B 17/56* (2006.01)

(52) U.S. Cl. ....................... 606/104; 606/305

(58) Field of Classification Search .................. 606/73, 606/104, 300, 305; 411/403, 410, 402, 404, 411/405, 407, 408; 81/451, 460, 448, 443, 81/125, 436, 467, 471
See application file for complete search history.

(56) References Cited

U.S. PATENT DOCUMENTS

| 2,268,515 | A | * | 12/1941 | Olson ........................... 81/460 |
| 2,317,319 | A | * | 4/1943 | West ............................ 81/438 |
| 3,409,058 | A | * | 11/1968 | La Pointe ..................... 81/448 |
| 3,498,351 | A | * | 3/1970 | Edwards et al. ............... 81/453 |
| 5,423,819 | A | * | 6/1995 | Small et al. .................... 606/73 |
| 5,649,931 | A | | 7/1997 | Bryant et al. |
| 6,398,785 | B2 | * | 6/2002 | Carchidi et al. ............... 606/73 |
| 7,249,544 | B2 | * | 7/2007 | Totsu .......................... 81/452 |

FOREIGN PATENT DOCUMENTS

| DE | 35 39 502 C1 | 2/1987 |
| DE | 38 04 749 A1 | 3/1989 |
| DE | 100 44 714 A1 | 4/2002 |
| FR | 2 723 839 A1 | 3/1996 |

* cited by examiner

*Primary Examiner*—Pedro Philogene
(74) *Attorney, Agent, or Firm*—McGlew & Tuttle, P.C.

(57) ABSTRACT

A system is provided with a screwdriver and a bone screw (30), wherein the screwdriver has a tool (4), which is provided with at least two radially and axially extending tool blades (5, 6, 7, 8), which can be caused to engage groove-like blade slots (36, 38) of the bone screw (30) in a positive-locking manner. To improve the handling of a bone screw (30) even in case of the smallest possible dimensions, provisions are made according to the present invention for the tool blades (5, 6, 7, 8) to form at least one elastic clamping section (20, 21, 22, 23), with which the tool (4) can be caused to clampingly engage the bone screw (30) in the area of the blade slots (36, 38).

20 Claims, 7 Drawing Sheets

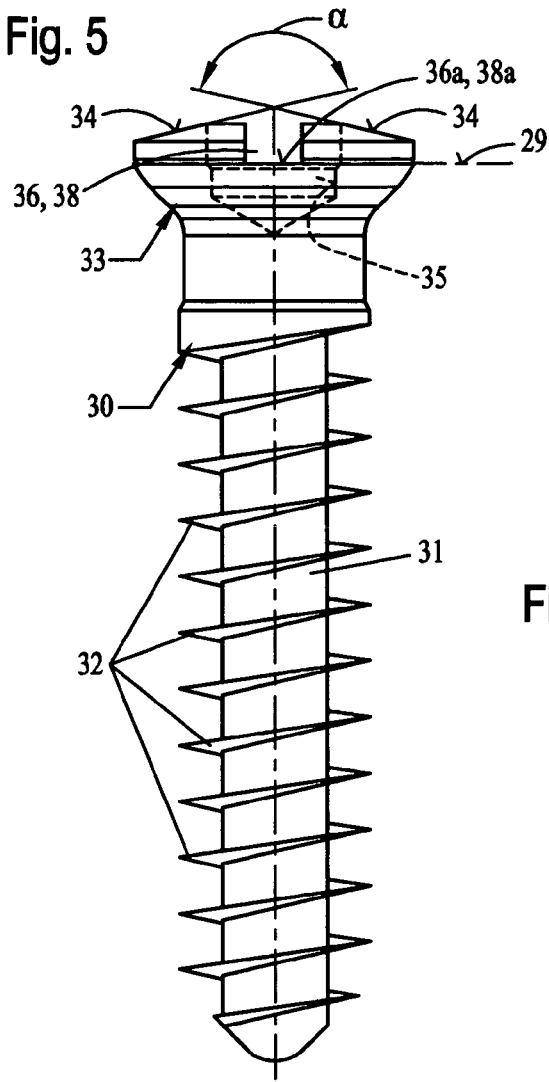
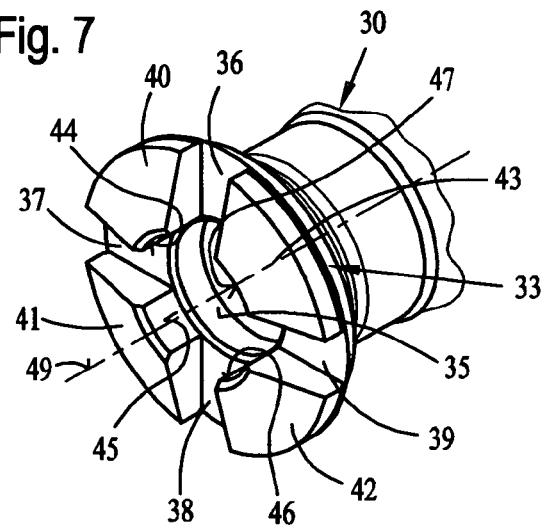
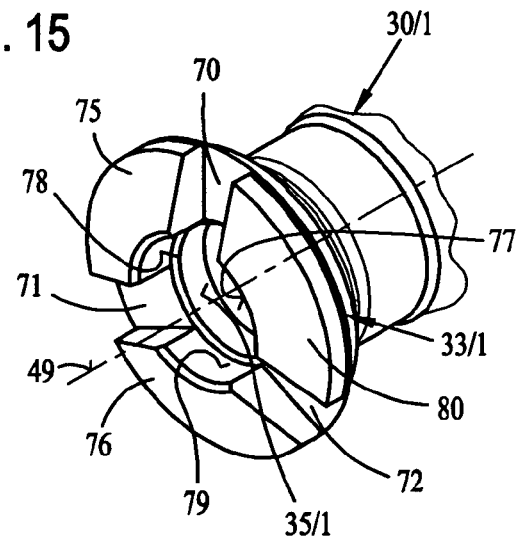
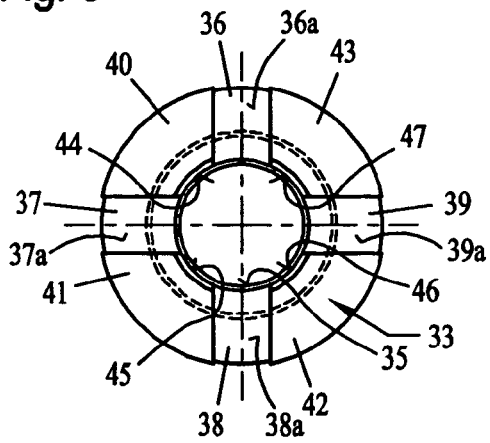
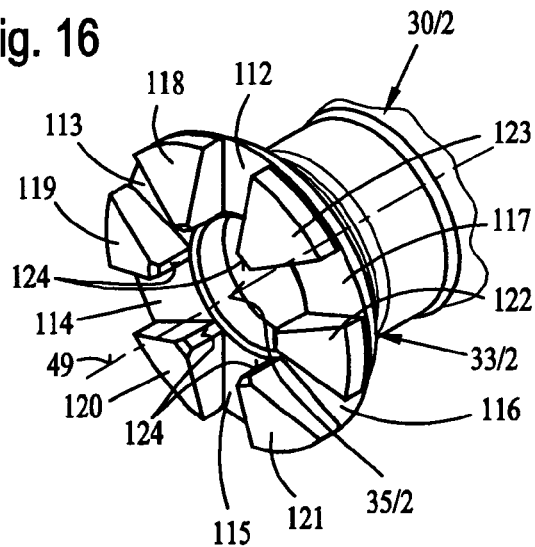

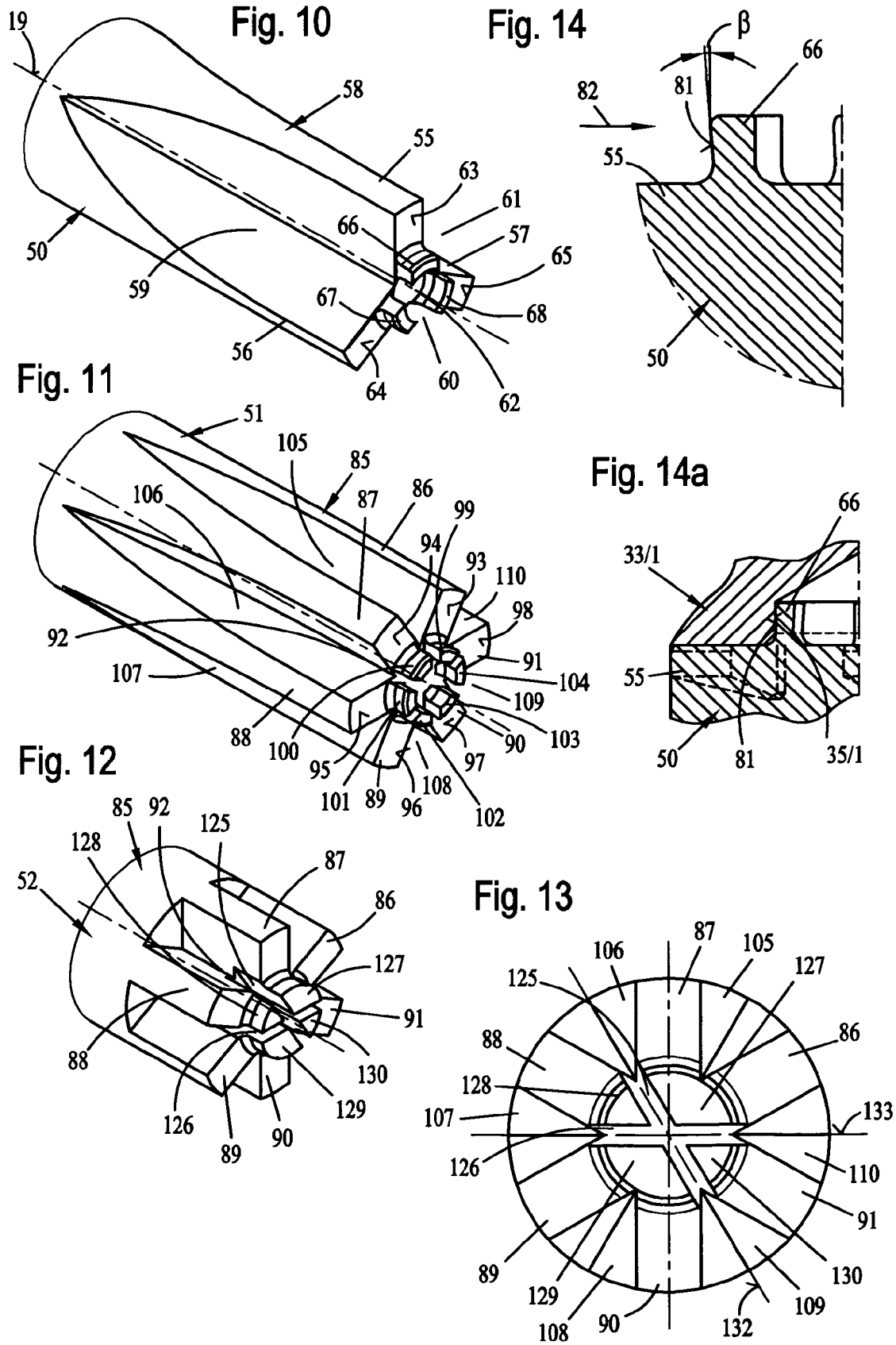

SYSTEM WITH A SCREWDRIVER AND A BONE SCREW

CROSS REFERENCE TO RELATED APPLICATIONS

This application claims the benefit of priority under 35 U.S.C. § 119 of German Application DE 20 2004 004 844.2 filed Mar. 27, 2004, the entire contents of which are incorporated herein by reference.

FIELD OF THE INVENTION

The present invention pertains to a system with a screwdriver and a bone screw, wherein the screwdriver has a tool, which is provided with at least two radially and axially extending tool blades, which can be caused to engage groove-like blade slots of the bone screw in a positive-locking manner.

BACKGROUND OF THE INVENTION

Bone screws are used, for example, for osteosynthesis either in conjunction with bone plates or also individually. Small fragment screws, in particular, also so-called cortex screws, are used after cranial injuries following accidents as well as in orthopedic maxillofacial surgery, in hand surgery and, in various dimensions, in other areas as well. Such small fragment screws are extremely difficult to handle because of their small dimensions. The length of such small fragment screws is approximately in the range of 8 mm to 10 mm, and the screw head may have a maximum diameter of about 3-4 mm and the screw shank may have a diameter of 1.5-2.5 mm. It is easy to imagine that such small fragment screws can be handled by means of a screwdriver with extreme difficulty only, because gripping by hand and attaching the screwdriver at the same time and the screwing in of such small fragment screws is difficult.

Various systems, by which the handling of such small fragment screws is said to be simplified, have now become known for making it possible to handle such small fragment screws in a simple manner at the site of use. Systems that are characterized, due to a special embodiment of the screwdriver, by the fact that the small fragment screws can be grasped by means of gripping elements at the screw head such that the small fragment screw or bone screw cannot slip off from the tool blades of the screwdriver any longer, have become known, for example, from U.S. Pat. No. 5,649,931, DE 38 04 749 A1, DE 100 44 714 C2, and DE 35 39 502 C1.

For example, a screwdriver is provided in the subject of DE 35 39 502 C1, which is provided with a tool, which is seated at a shank and has a plurality of tool blades, with which the tool can be caused to engage corresponding blade slots of the screw head of the bone screw in a positive-locking manner. Furthermore, a screw removal means, which has a gripping member, by means of which a screw head can be grasped, is provided at the shank. This gripping member is actuated by means of a clamping sleeve displaceable along the shank, wherein the gripping members elastically project from the shank radially in the outward direction when the clamping sleeve is retracted. When the clamping sleeve is displaced in the direction of the tool seated at the end of the shank, the gripping members are pressed by the clamping sleeve radially inwardly, so that these essentially hook-shaped gripping members extend behind the screw head and the latter is held snugly against the tool at the end of the shank. The subjects of the other documents mentioned above have a similar embodiment as well.

It has now been found that the handling of such special screwdrivers is to complicated insofar as these screwdrivers must first be placed with the tool blades of their tool on the screw head and the clamping sleeve must subsequently be displaced along the shank in order to grasp the screw head of the bone screw. Since the hook-shaped gripping members extend behind the screw head, it is not possible with this tool to screw in a bone screw completely. Shortly before the maximum screwing-in depth is reached, the clamping sleeve must be retracted again in order to release the screw head. The gripping members also must be subsequently retracted axially, so that they are not in contact with the bone when the bone screw is screwed in further and the further, complete screwing in of the bone screw is not hindered. At the same time, the gripping members must be withdrawn from their position in which they project axially over the tool in order not to hinder the complete screwing in. However, if the clamping sleeve is brought into an inactive position together with the gripping members, the screwdriver with its blade-like tool can slip off, as a result of which the safety of operation is diminished.

DE 296 11 140 U1 discloses a system comprising a screwdriver and a bone screw, in which the tool of the screwdriver has a central hexagon, which is arranged between two radially outwardly directed tool blades. This hexagon minimally projects over the tool blades in the axial direction and can be caused to engage a corresponding hexagon socket of the bone screw. The hexagon of the tool has a conical shape, so that this hexagon is clampingly accommodated in the hexagon socket of the bone screw when it is correspondingly pressed against the bone screw. The drawback of this embodiment is that after the hexagon of the tool has been inserted several times into a hexagon socket of the bone screw, a burr is formed at the hexagon of the tool, so that this tool is no longer able to function after several uses, because it can no longer be inserted into the hexagon socket of the bone screws deep enough, but is in contact with the burr. However, a clamping hold also cannot thus be achieved any longer.

Clamping elements, which are mounted elastically as separate components at the tool, are used in the subject of DE 93 10 668.8. On the one hand, a clamping ball is provided here, which is inserted into a hole of the tool. A hexagon socket or even a hexagon insert bit may be provided here as the tool. It is disadvantageous here that this embodiment cannot be used in case of extremely small bone screws, because the clamping elements must always have an extremely small axial distance from the outer front side of the tool. The consequence of this is that the bone screws would have to have a correspondingly long hexagon insert bit or hexagon socket to enable the clamping element to clampingly engage the bone screw at all. However, a great axial length of the hexagon insert bit or hexagon socket is not possible in case of extremely small bone screws, because the dimensions of these screws must be extremely small for use in microsurgery.

DE 91 10 576 U1 describes a screwdriver, in which a spring bar, which is to be clampingly engaged with the blade slots of the bone screw by its radial spring force, is provided within the tool shank. The handling of this design is also extremely uncertain, because reliable clamping cannot always be achieved. In addition, this design cannot be embodied in the case of the aforementioned extremely small bone screws, because the tool shank, with its extremely small diameter, does not permit the arrangement of such a spring bar.

The subject of FR 2 723 839 is likewise unsuitable for small bone screws. A clamping cylinder projecting from the tool on the front side is provided here. This clamping cylinder has a cross slot, which is joined by outwardly radially projecting tool blades. The clamping cylinder is pressed here into an axial hole of the tool. In case of tool shanks of a small diameter, this is likewise not possible, because the stability of the tool would be compromised.

SUMMARY OF THE INVENTION

Consequently, the object of the present invention is to provide a system comprising a bone screw and a screwdriver, with which the handling of a bone screw is considerably simplified and which can also be embodied in the case of extremely small dimensions.

The object is accomplished according to the present invention, together with the features of the preamble, in that the tool blades form at least one elastic clamping section, with which the tool can be caused to clampingly engage the bone screw in the area of the blade slots. Due to this embodiment, the clamping elements proper are formed by the tool blade itself, so that the tool can also be reliably embodied in case of small dimensions. In particular, both the tool and the bone screw belonging to the system with its coupling elements can be provided with sufficient stability.

Furthermore, unlike in the state of the art described in the introduction, additional manipulations of the screwdriver to hold the bone screw with its screw head snugly at the screwdriver, on the one hand, and to again eliminate this connection, on the other hand, become superfluous. Furthermore, it is advantageous due to the special embodiment according to the present invention that the operator does not need to take any further actions, for example, a pulling back of a clamping sleeve or the like, to make it possible to screw the bone screw in completely.

To ensure the centered, clamping hold of the tool at the bone screw, provisions may be made for the blade slots of the bone screw to open in a central, cylindrical axial hole, and for the clamping sections of the tool blades to be formed from elastically flexible clamping elements, which project axially from the front surfaces of the tool blades and whose clamping surfaces are located on an external diameter that is adapted to the diameter of the axial hole to achieve a clamped connection.

Due to this embodiment according to the present invention of both the screw head of the bone screw and the tool of the screwdriver, the bone screw can be handled in a very simple manner. The screw head has, for this purpose, a cylindrical axial hole between its blade slots, into which axial hole the blade slots open. The screwdriver is in turn provided with corresponding tool blades, which fittingly engage the blade slots of the screw head in a positive-locking manner. Each of the tool blades has a clamping element each, which axially projects over the front surface of the respective tool blade and with which the screwdriver can be caused to engage the cylindrical axial hole of the screw head when attached to the screw head. The external diameter of these elastic clamping elements is selected to be such that a clamped connection is achieved between the clamping elements and the axial hole.

For handling, this means that the screwdriver according to the present invention with the tool blades and the clamping elements of its tool can be attached to the screw head centered in a simple manner, and a clamped connection, which holds the screw head firmly at the tool, is formed at the same time at the time of the attachment. A bone screw of the type according to the present invention can thus be removed from a magazine in a simple manner with the screwdriver of the type according to the present invention and can then be screwed into a bone just as simply at the site of use. The clamping forces are selected to be such that after the bone screw has been screwed in, the screwdriver with its tool and its clamping elements can be pulled off from the screw head of the bone screw in the axial direction in a very simple manner.

Provisions may be made for the inner limiting surfaces of the ring sectors formed by the blade slots, which said limiting surfaces are located between the individual blade slots, to form partial surfaces of a cylinder, whose diameter is larger than the diameter of the axial hole by a factor of 0.05 to 0.2. Sufficient clamping force is achieved due to this embodiment.

The axial front surfaces of the ring sectors may form partial surfaces of the envelope of a cone, whose cone angle is between 145° and 160°. Due to this embodiment, it is also possible to attach the tool to the bone screw "obliquely."

Furthermore, provisions may be made for the axial center planes of the blade slots to intersect in the axis of the screw, in which case the width of the blade slots corresponds to approximately one fifth of the screw head diameter. The elastic flexibility of the clamping sections can be adapted due to this embodiment to the existing requirements, and sufficient stability of the bone screw is preserved due to the width of the blade slots.

Provisions may be for the diameter of the central axial hole to correspond to approximately one third of the screw head diameter and for the depth of the axial hole to be able to correspond to one tenth to one eighth of the screw head diameter. Centered attachment of the corresponding tool with its axially projecting clamping elements is reliably guaranteed due to this embodiment.

The tool blades of the screwdriver may be formed by uniform cutouts of a rotationally symmetrical blade shank, which said cutouts have a triangular cross section, and may be connected with one another in one piece by a central shank core, and at least one of the tool blades is provided with a separating slot and forms a clamping element located radially on the outside. Extremely simple manufacture of the clamping element is achieved due to the separating slot in the tool blade even in case of extremely small sizes, and a clamping hold of the tool in the blade slots of a bone screw is ensured. The separating slot may also be arranged such that it extends tangentially to the core of the tool in more than two tool blades, so that two of the tool blades are connected with one another in one piece and they transmit the rotating forces to the bone screw, while the clamping forces are brought about by the "slotted" tool blade, because this is arranged such that it is slightly offset in relation to the corresponding blade slot of the bone screw in the circumferential direction.

Furthermore, the clamping elements may comprise sectors of a circular ring that is concentric with the axis of the blade shank, in which case the sectors of the circular ring are formed by the cutouts that form the tool blades. Extremely simple manufacture of the clamping elements is achieved due to this embodiment.

Similarly advantageously is also the embodiment according to which provisions may be made for the clamping elements to comprise sectors of a circular ring, which are located on the front surface of a tool blade and are formed by radially extending grooves.

The clamping elements may comprise the circular sectors of a central cylindrical pin, which may be formed by at least two intersecting, diametrically extending grooves, which are open on the front side and radially, in which case they may penetrate the shank core and have an axial depth that is at least twice the axial height of the clamping elements. Provisions may be made here for the grooves to be located in the planes of symmetry of two diametrically opposite cutouts. Due to this embodiment, the clamping elements acquire an additional elastic flexibility in the radial direction.

The shank core may now have a diameter that is at least equal to the diameter of the pin from which the circular sectors are formed, as a result of which the manufacture and the stability are improved.

Furthermore, provisions may be made for fewer circular sectors than tool blades to be present, in which case two diametrically opposite tool blades of six tool blades have separate circular sectors on their front surfaces and the front surfaces of two tool blades located between them in the circumferential direction together carry one circular sector.

Provisions may be made for the clamping elements to have circumferential surfaces tapering conically toward the plane of the front surfaces of the tool blades by 2° to 6° and to have a beveled or rounded marginal edge. The clamping action of the clamping elements is improved by this embodiment in the axial hole of the bone screw.

Provisions may be made for at least one of the tool blades to have, at least in its axially outer end area engaging the blade slots, a course deviating from the course of the blade slots in such a way that the tool blades can be caused to clampingly engage the blade slots. This means that the tool blades may have an arc-shaped course, for example, in case of blade slots of the bone screw that extend radially linearly. The width of the tool blades approximately corresponds here to the width of the blade slots of the bone screw. When the tool blades are attached to the blade slots, a slight elastic deformation of the tool blades takes place, so that the tool blades are held clampingly in the blade slots and the bone screw may thus be held at the screwdriver or its tool in a simple manner. The tool blade thus forms a clamping element itself because of its shape and has a correspondingly dimensionally stable and elastic design.

Due to this embodiment, axially projecting clamping elements at the tool blades as well as a central axial hole in the bone screw can be dispensed with, especially in case of small sizes.

Furthermore, an angular offset of one of the tool blades may be provided in the circumferential direction, so that this tool blade is arranged slightly offset in the circumferential direction in relation to the corresponding blade slot of the bone screw, while the angular orientations of the other tool blades provided coincide with those of the respective corresponding blade slots.

One of the tool blades may also be arranged offset in the circumferential direction in parallel to a direction of radial extension, while the other tool blades provided are directed such that they coincide with the corresponding blade slots. One of the tool blades may also be provided with a groove arranged on the front side, for example, in the radially outer area, so that the tool blade forms an outer clamping element. If, for example, four tool blades are provided, two tool blades located diametrically opposite may be provided with such a groove, so that symmetrical clamping and consequently reliable holding of the tool at the bone screw is brought about.

The deviation in shape may be extremely small here and be in the range of 0.025 mm to 0.25 mm. This slight deviation in shape is sufficient for a sufficient press fit, on the one hand, and, on the other hand, the tool blades are deformed elastically only slightly on insertion into the blade slots, so that the tool blades do not suffer any permanent deformation. The amount of the deviation in shape depends on the overall size of the tool blades as well as the bone screw to be actuated.

Furthermore, provisions may be made for the tool to have a central shank core, which is provided with one or more axial recesses, which separate the tool blades at least in their end areas that can be caused to engage the blade slots. This embodiment can be provided especially in case of tools with three or more tool blades. The elastic properties of the tool blades are guaranteed by this axial recess.

Provisions may be made for the recess to be formed from a central blind hole, which is prepared in the shank core on the front side and has an axial depth of 0.5 mm to 2.5 mm starting from the axially outer front surfaces of the tool blades. Extremely simple possibility of manufacture is achieved due to this embodiment. The axial depth of about 0.5 mm to 2.5 mm is selected essentially as a function of the overall size of the tool blades, especially the radial length and the width of these tool blades. In case of larger dimensions of the tool blades, the axial depth of the recess may assume a higher value, and it may assume a lower value in case of small dimensions of the tool blades. The dimensional stability of the tool blades, which decreases with increasing depth, on the one hand, and, on the other hand, the elasticity of the tool blades, which increases with increasing depth, is affected by the axial depth.

As an alternative, the recesses may also be formed from radially extending grooves, which have an axial depth of 0.5 mm to 2.5 mm starting from the axially outer front surfaces of the tool blades. The mode of action of these recesses formed in this manner is identical to that described as to another embodiment, but the manufacture may be more advantageous, especially in case of an even number of tool blades.

To simplify the attachment of the tool blades to the blade slots or to the bone screw, provisions may be made to provide, in the area of the shank core, a centering pin, which axially projects over the tool blades and whose diameter is larger than the shank core, and for the centering pin to engage a central axial hole of the bone screw in the state in which the tool is attached to the bone screw.

"Angle errors" occurring during the screwing in of a bone screw manually are compensated. An angle error is defined here as a non-coaxial orientation of the tool shank in relation to the central longitudinal axis of the bone screw to be screwed in. Certain "wobblings" of the screwdriver, which are effectively compensated by the special shape of the tool blades, on the one hand, and of the blade slots, on the other hand, always occur during the manual actuation of the screwdriver by hand. Provisions may be made for this purpose for the axially outer front surfaces of the tool blades to extend obliquely outwardly, set back linearly or in an arc-shaped pattern, starting from the shank core, at a cone angle δ of 3° to 10° in relation to a plane extending at right angles to the central longitudinal axis of the shank core, and for the bases of the corresponding blade slots of the bone screw to have the same course.

Due to the embodiment of the present invention according to one of the above patent claims individually and in their combination, a system comprising a bone screw and a screwdriver is made available, which can be handled reliably in an extremely simple manner by the tool of the screwdriver being able to be connected with and again detached from the bone screw according to the present invention by a clamping plug-in connection brought about by clamping elements of the tool. Parts of the tool blades themselves, which may be radially extending sections of the tool blade and/or also be designed as a kind of a divided centering pin, which is made integral in one piece with the tool blades, projecting axially, are provided as clamping elements here.

The present invention will be explained in greater detail below on the basis of the drawings. The exemplary embodiments described below are used only as examples to explain the present invention. The various features of novelty which characterize the invention are pointed out with particularity in the claims annexed to and forming a part of this disclosure.

For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a side view of a bone screw according to the present invention, which can be actuated with the tool of the screwdriver from FIG. 1;

FIG. 6 is a top view of the screw head of the bone screw from FIG. 5;

FIG. 7 is a perspective view of the screw head from FIG. 6;

FIG. 10 is a second exemplary embodiment of a tool with three tool blades;

FIG. 11 is another exemplary embodiment of a tool with six tool blades;

FIG. 12 is an exemplary embodiment of a tool with likewise six tool blades and a total of four clamping elements;

FIG. 13 is a top view XIII of the tool from FIG. 12;

FIG. 14 is a partial section through a clamping element of the tool from FIG. 10;

FIG. 14a is the clamping element from FIG. 14 engaging the screw head from FIG. 15;

FIG. 15 is a perspective view of a screw head with three radial slots, which can be caused to engage the tool from FIG. 10;

FIG. 16 is a perspective view of a screw head, which is provided with a total of six radial slots and which can be caused to engage the tool from FIG. 11 or the tool from FIG. 12 as desired;

DESCRIPTION OF THE PREFERRED EMBODIMENTS

Figure 1:
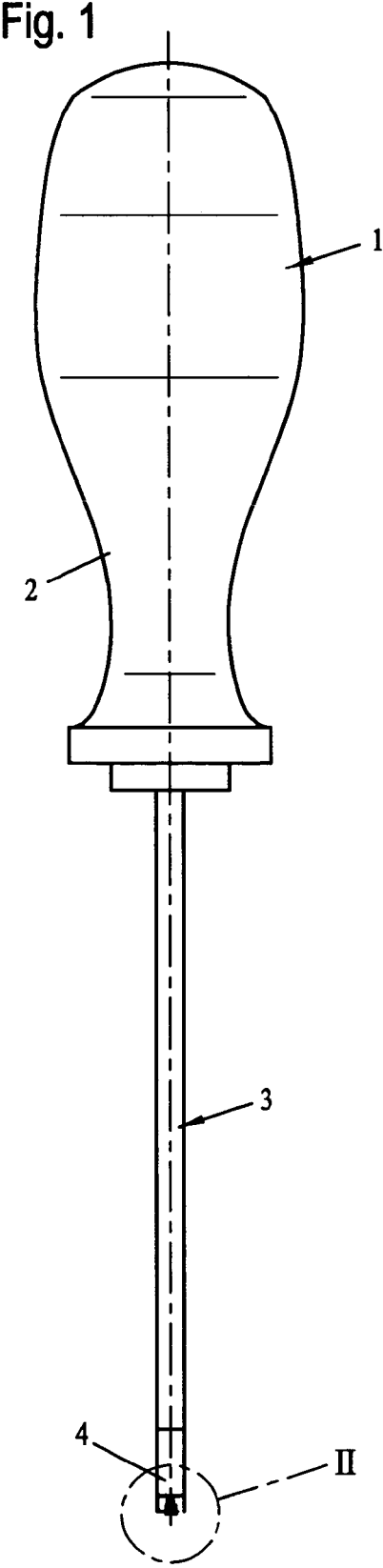
FIG. 1 is a side view of a screwdriver with an exemplary embodiment of a tool according to the present invention.

Referring to the drawings in particular, FIG. 1 shows a side view of a screwdriver 1, which has a grip part 2 for actuation in the known manner. This grip part 2 is on connection with a tool shank 3 in such a way that they rotate in unison, the tool shank having, at its end located opposite the grip part 2, a tool 4, which is used to rotatingly actuate a bone screw. Provisions may be made here for the tool shank 3 to be attached to the grip part 2 such that it can be replaced with other tool shanks with different tools.

Figure 2:
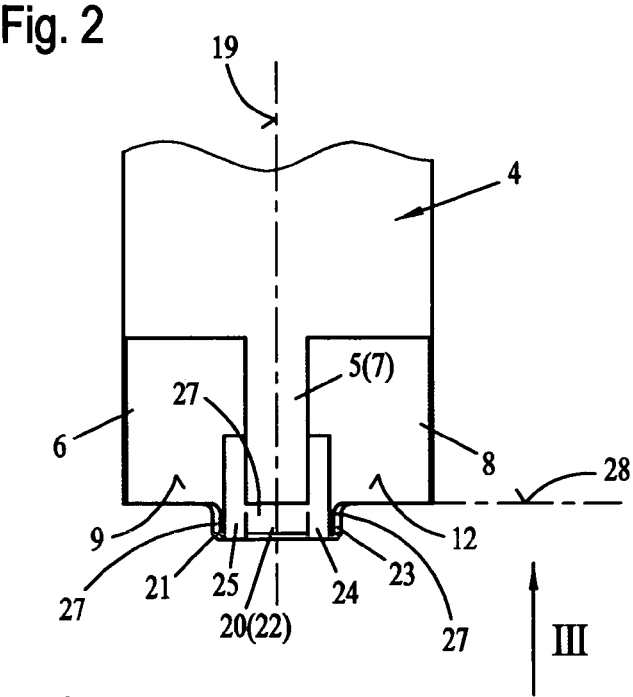
FIG. 2 is an enlarged detail II of the tool of the screwdriver from FIG. 1.
Figure 3:
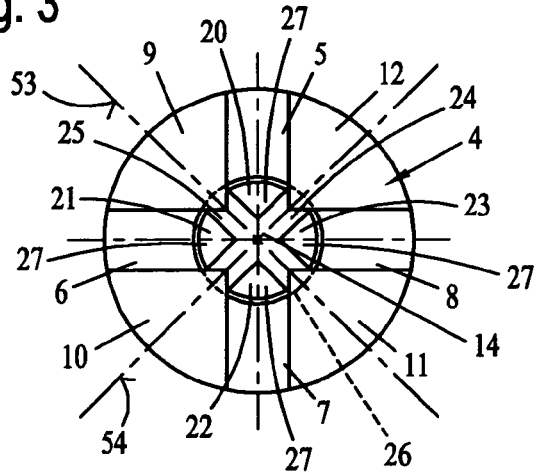
FIG. 3 is a front view III of the tool from FIG. 2.

FIG. 2 shows an enlarged view II of this tool 4 from FIG. 1, and it can be recognized in connection with FIG. 3 that this tool 4 has a total of four radially extending tool blades 5, 6, 7 and 8. These four tool blades 5 through 8 are formed by cutouts 9, 10, 11 and 12 which have an essentially triangular cross section.

Figure 4:
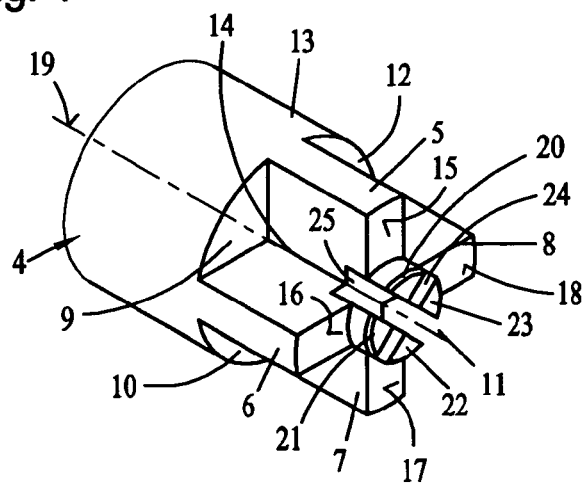
FIG. 4 is a perspective view of the tool from FIGS. 2 and 3.

As is apparent from FIGS. 3 and 4, the tool 4 forms a rotationally symmetrical, cylindrical blade shank 13, in which the cutouts 9 through 12 are arranged. Furthermore, it can be recognized from FIGS. 3 and 4 that the tool blades 5 through 8 are connected with one another in one piece by a central shank core 14. The tool blades 5 through 8 are of a web-like design each and end in the axial direction with their respective, flat front surfaces 15, 16, 17 and 18 in a common plane 28, which extends at right angles to the central longitudinal axis 19 of the tool 4, as this can be recognized especially from FIG. 2.

A clamping element 20, 21, 22 and 23 each, which project over the respective front surfaces 15 through 18 outwardly in the axial direction, are provided on each of the front surfaces 15 through 18 of each tool blade 5 through 8. These clamping elements 20 through 23 are formed in this exemplary embodiment by two diametrically extending grooves 24 and 25, which intersect each other at right angles and are open on the front side and radially. In other words, the clamping elements 20 through 23 in this exemplary embodiment of the tool 4 comprise four cylinder sections 27 of a central, cylindrical pin 26, which is indicated by broken lines in FIG. 3. The axial depth of the two grooves 24 and 25 is made greater than the axial height of the four clamping elements 20 through 23, so that the two grooves 24, 25 extend in the axial direction into the shank core 14 of the blade shank 13. Furthermore, as can be recognized from FIG. 3, the grooves 24, 25 are located in the respective planes of symmetry 53 and 54 of two cutouts 9, 11 and 10, 12 located diametrically opposite each other. The central pin 26 forming the clamping elements 20 through 23 has a diameter that is larger than the diameter of the shank core 14 in this exemplary embodiment.

FIG. 5 shows as an example a bone screw 30, which can be actuated by means of the tool 4 and which is provided with a threaded shank 31 with the external thread 32, which has a diameter of about 2 mm. This external thread 32 is designed as a tapping thread in this exemplary embodiment.

A screw head 33, which is radially expanded and has a diameter of about 3 mm, is made integral in one piece with the top end of the threaded shank 31 in FIG. 5. The upper front surface 34 of the screw head 33 forms a kind of envelope of a cone, whose cone angle α is between 145° and 160°. It can also be recognized from FIGS. 5 and 6 that the screw head 33 has a central, cylindrical axial hole 35, which is designed as a blind hole. The screw head 33 is provided in this exemplary embodiment with a total of four radially extending blade slots 36, 37, 38 and 39, which have a depth increasing radially from the outside to the inside corresponding to the cone angle α provided because of the "conical shape" of the outer front surface 34 of the screw head 33.

These blade slots 36 through 39 open, as this is apparent especially from FIG. 7, into the axial hole 35. Ring sectors 40, 41, 42 and 43, whose number equals a total of four in this exemplary embodiment, are formed by the blade slots 36 through 39. The diameter of the partial surfaces 44, 45, 46 and 47 formed by these ring sectors toward the axial hole 35 is made larger than the diameter of the axial hole 35 by a factor of 0.05 to 0.02. The blade slots 36 through 39 have a U-shaped cross-sectional shape each with a respective base 36a, 37a, 38a and 39a (FIG. 6), which extend at right angles to the central longitudinal axis 49 of the bone screw 30 and are located in a common plane 29 (FIG. 5). The axial depth of the axial hole 35 starting from the common plane 29 of the bases 36a through 39a may be equal to or greater than the maximum axial depth of the blade slots 36 through 39 of the screw head 33. Furthermore, provisions may also be made for the depth of the axial hole 35 to correspond to at least one tenth to one eighth of the diameter of the screw head 33.

This embodiment of the screw head 33 with its blade slots 36 through 39 and with its axial hole 35 as well as with the radially expanded partial surfaces 44 through 47 makes it possible to attach the tool 4 with its clamping elements 20 to 23 to the axial hole 35 in a simple manner.

It is easy to imagine that when the tool 4 is attached to the screw head 5, the tool can be caused, on the one hand, to engage the blade slots 36, 37, 38 and 39 of the screw head in a positive-locking manner. Furthermore, the clamping elements 20 through 23 will clampingly engage the axial hole 35 when the tool 4 is attached to the screw head 33.

The external diameter of the clamping elements 20 through 23 is adapted here to the internal diameter of the axial hole 35 such that a clamping fit of the clamping elements 20 through 23 in the axial hole 35 is achieved. This means that after the tool 4 has been attached to the screw head 33, the bone screw 30 is held clampingly and consequently captively at the tool 4 by means of the axial hole 35 of its screw head 33. Since the dimensions of both the axial hole 35 and the clamping elements 20 through 23 are coordinated with one another in terms of their axial lengths such that the tool blades 5 through 8 will reliably engage the blade slots 36 through 39 in a positive-locking manner, reliable actuation of the bone screw 30 is thus guaranteed.

Figure 8:
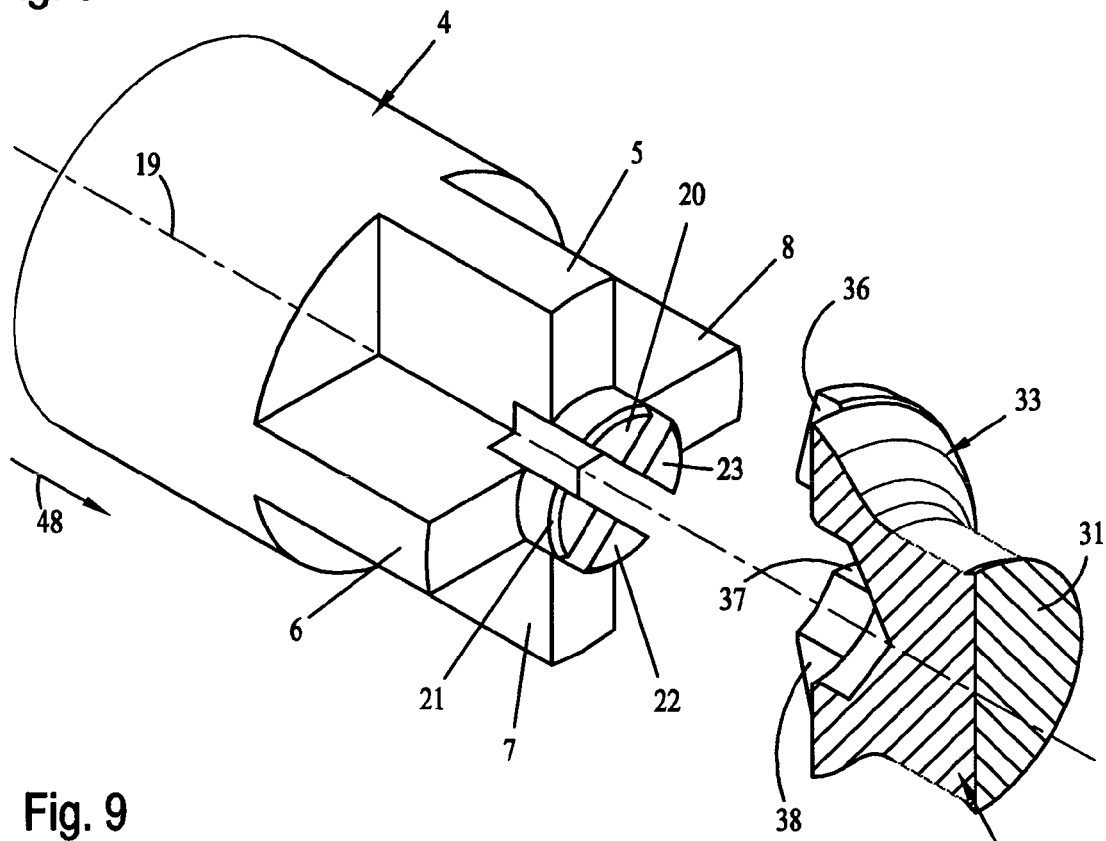
FIG. 8 is a perspective view of the tool from FIG. 4 together with a partial section of the rear view of the screw head from FIG. 7.

FIG. 8 shows an enlarged view of the tool 4, and the tool blades 5 through 8 are directed here toward the screw head 33, which is shown in the partial section and is viewed from the screw shank 31. In this orientation, the tool blade 5 is directed toward the blade slot 36, the tool blade 8 toward the blade slot 39, the tool blade 7 toward the blade slot 38, and the tool blade 6 toward the blade slot 39, which is not visible in FIG. 8.

Figure 9:
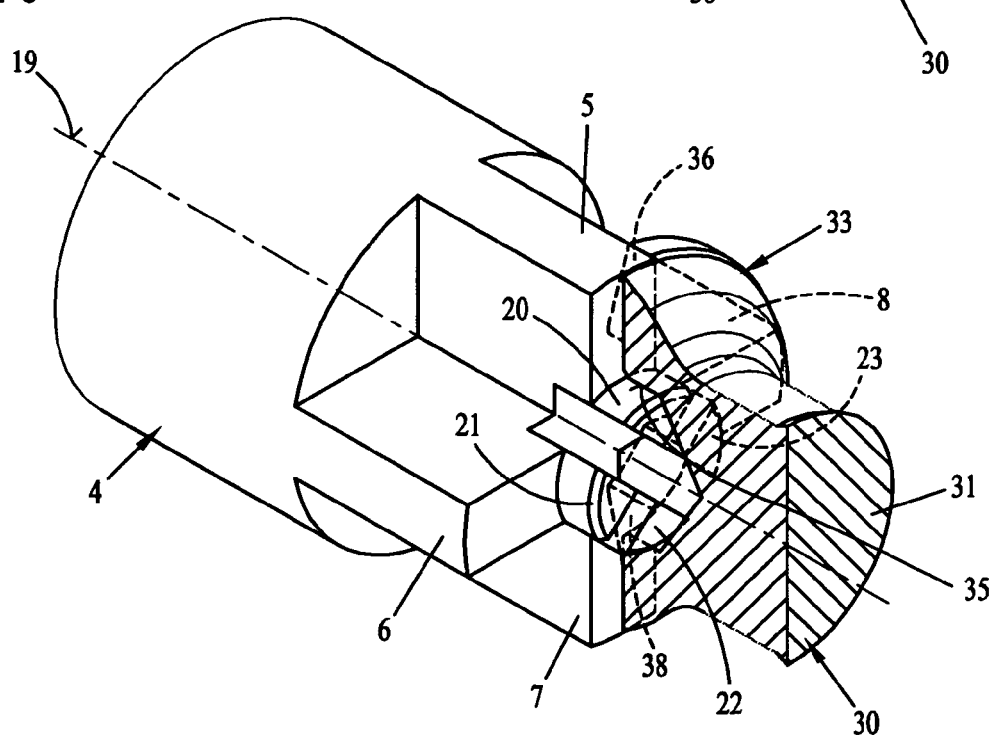
FIG. 9 is the screw head from FIG. 8 engaging the tool from FIG. 8.

If the tool 4 is now brought into contact with the screw head 33 by movement in the direction of the arrow 48 in the axial direction, the tool blades 5 through 8 will enter the corresponding blade slots 36 through 39 of the screw head 33 in a positive-locking manner, as this is apparent from FIG. 9. At the same time, the four clamping elements 20 through 23 enter the axial hole 35, in which these clamping elements 20 through 23 are held clampingly because of their slight radial oversize. It is easy to imagine that because of this combination of the clamping elements 20 through 23, the screw 30 with its screw head 33 is held clampingly at the tool 4. The bone screw 30 can thus be removed from a corresponding screw magazine in a simple manner, on the one hand, and it can also be screwed reliably into a bone, on the other hand.

Other exemplary embodiments of tools 50, 51 and 52 are shown in FIGS. 10 through 13.

FIG. 10 shows a tool 50, which has a total of three radially extending tool blades 55, 56 and 57. The tool 50 is likewise formed by a cylindrical blade shank 58, which is provided with three cutouts 59, 60 and 61 to form the three tool blades 55, 56 and 57. The three tool blades 55, 56 and 57 are also connected with one another in one piece via a shank core. Radially outside the shank core 62, the three front surfaces 63, 64 and 65 of the three tool blades 55, 56 and 57 are provided with an axially projecting ring sector 66, 67 and 68 each, which are designed as sectors of a circular ring (not explicitly shown in the drawing) concentric with the longitudinal central axis 19 of the blade shank 58.

The ring sectors 66, 67 and 68 are likewise formed by the three cutouts 59, 60 and 61 of the blade shank 58. The ring sectors 66, 67 and 68 are the clamping elements of the tool 50 here, which can be caused to engage a correspondingly embodied screw head 30/1, as this is shown in FIG. 15. These ring sectors 66, 67 and 68 also form a kind of centering pin at the same time.

The screw head 30/1 likewise has a central axial hole 35/1 for this purpose. Furthermore, this screw head 33/1 is also provided in this exemplary embodiment with a total of three radially extending blade slots 70, 71 and 72, which open into the axial hole 35/1. Ring sectors 75, 76 and 77, which are limited toward the axial hole 35/1 by partial surfaces 78, 79 and 80 extending in an arc-shaped pattern, are likewise formed by the blade slots 70, 71 and 72 on the front side at the screw head 30/1. The internal diameter of the partial surfaces 78, 79 and 80 lying on the same diameter is likewise made larger here than the diameter of the axial hole 35/1 by a factor of 0.05 to 0.2.

Thus, this embodiment corresponds identically to the embodiment of the screw head of the screw 30 from FIG. 5, except for the fact that only three blade slots 70 through 72 are provided here. The dimensions, especially the external diameter of the ring sectors 66, 67 and 68 in the sense of the clamping elements 20 through 23 is selected here to be such that these clamping elements 66, 67 and 68 can be caused to clampingly engage the axial hole 35/1 of the screw head 33/1.

At the same time, the three tool blades 55, 56 and 57 will engage the blade slots 70, 71 and 72 in a positive-locking manner, so that the screw 30/1 is held clampingly at the tool 50, on the one hand, and it can be reliably actuated, on the other hand.

The anterior front surfaces 63, 64 and 65 of the tool blades 55, 56 and 57 are also located in a common plane (not explicitly shown in the drawing), which extends at right angles to the central longitudinal axis 19 of the blade shank 58.

FIG. 14 shows a longitudinal section through the clamping element 66, which is joined radially outwardly by the tool blade 55. As is apparent from FIG. 14, the outer jacket surface 81 of this clamping element 66 extends such that it expands radially at an angle β of about 4° toward the axially outer end starting from the tool blade 55. Because of the extremely small cross section of the clamping element 66, this clamping element is readily flexible in the radial direction, so that the clamping element 66 is pressed slightly in the direction of the arrow 82 when it is being pushed into the axial hole 35/1 and a clamping hold is thus achieved in the axial hole 35/1, as this is shown in FIG. 14a. This embodiment of the clamping element 66 also applies to the clamping elements 67 and 68.

In the exemplary embodiment of the tool 51, the blade shank 85 is provided with a total of six tool blades 86, 87, 88, 89, 90 and 91, which likewise extend radially starting from a central shank core 92. On their respective front sides 93, 94, 95, 96, 97 and 98, these tool blades 86 through 91 likewise have clamping elements 99, 100, 101, 102, 103 and 104, which have a design identical to that of the clamping elements 66 through 68 of the tool blades 63 through 65 in FIG. 10, which are embodied as ring sectors, aside from their circumferential length.

This means that corresponding cutouts 105, 106, 107, 108, 109 and 110 are provided in the blade shank 85 as well, and these cutouts form the tool blades 86 through 91, on the one hand, and the clamping elements 99 through 104, which are likewise designed as ring sectors, on the other hand.

The tool 51 with its tool blades 86 through 91 can be caused to engage corresponding blade slots 112, 113, 114, 115, 116 and 117 of a correspondingly embodied screw head 33/2 of a bone screw 30/2 in a positive-locking manner. Such a screw head 33/2 is shown as an example in FIG. 16.

Ring sectors 118, 119, 120, 121, 122 and 123 are likewise formed on the screw head 33/2 by these blade slots 112 through 117. The blade slots 112 through 117 likewise open into an axial hole 35/2, which can be caused to be clampingly engaged by the clamping elements 99 through 104. The inner partial surfaces 124 of the ring sectors 118 through 123 are likewise on a diameter that is larger than the diameter of the axial hole 35/2 by a factor of 0.05 to 0.2.

It is easy to imagine that the tool 51 with its tool blades 86 through 91 can be caused to engage the blade slots 112 through 117 of the screw head 33/2 in a positive-locking manner, as this was described in FIGS. 8 and 9 in connection with the exemplary embodiment of the tool 4 together with the screw head 33.

At the same time, the clamping elements 99 through 104, designed as ring sectors, will clampingly engage the axial hole 35/2, so that the screw 30/2 is held at the tool 51 via its screw head 33/2.

FIG. 12 shows an alternative embodiment of a tool which has a design similar to that of the tool 51 in FIG. 11.

Six radially extending tool blades 86 through 91 are likewise provided in the tool 52. These tool blades 86 through 91 are formed by six cutouts 105 and 110 here as well, which have a design corresponding to that of the cutouts 9, 10, 11 and 12 in the exemplary embodiment shown in FIGS. 2 through 4. However, the clamping elements provided here are not ring sectors according to the exemplary embodiment shown in FIG. 11, but clamping elements 127, 128, 129 and 130 formed by two diametrically extending grooves 125 and 126. Due to the arrangement of the grooves 125 and 126, the two clamping elements 127 and 129 are a common part of the two tool blades 86, 87 and 89, 90, respectively. The two clamping elements 128 and 130, whose circumferential extension is smaller, are associated with the respective tool blades 88 and 91.

More stable clamping elements are obtained due to this embodiment, especially because of the greater circumferential length of the two clamping elements 127 and 129, so that an unacceptable deformation of these clamping elements during the attachment to the screw head 33/2 in FIG. 16 is reliably prevented from occurring. Due to the fact that the tool blades 86, 87 and 89, 90 are connected with one another in the area of the shank core 92, these tool blades 86, 87, 89, 90 acquire greater strength, so that they cannot be deformed even in case of stronger rotating forces during the screwing in of a bone screw.

FIG. 13, which shows a front view of the tool 52, shows the exact arrangement of both the tool blades 86 through 91 and of the clamping elements 127 through 130 in greater detail. It can be recognized that the grooves 125, 126 are located each in the respective planes of symmetry 132 and 133 of two cutouts 106, 109 and 107, 110 located diametrically opposite, as this was described in greater detail in connection with the exemplary embodiment shown in FIGS. 2 through 4. The grooves 125 and 126 correspondingly also extend in the axial direction into the shank core 92 of the blade shank 85, as this can be recognized from FIG. 12.

Provisions may also be made here for the tool blades 86 through 91 to be designed without the clamping elements 127 through 130. The two "individual" tool blades 88 and 91 are to be arranged with a slight offset in the circumferential direction in this case, so that these two tool blades 88 and 91 will themselves form the clamping elements if the blade slots 114 and 117 of the corresponding bone screw 30/2 from FIG. 16 are not arranged offset in the circumferential direction.

Figure 17:
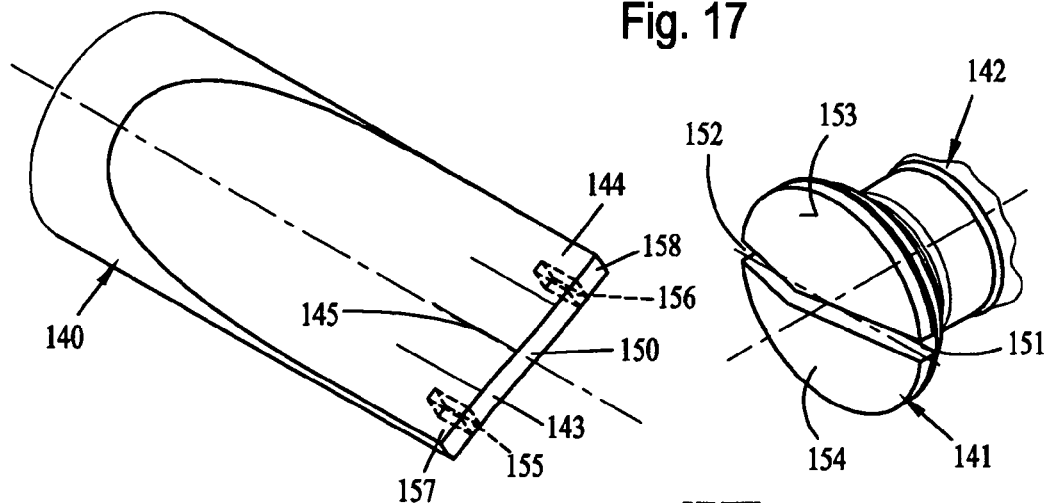
FIG. 17 is a perspective view of another exemplary embodiment of a tool together with a bone screw belonging to it.

FIG. 17 shows a perspective view of another exemplary embodiment of both a tool 140 and a corresponding screw head 141 of a bone screw 142.

The tool 140 has two approximately diametrically opposite tool blades 143 and 144, which extend approximately radially starting from a shank core 145, which cannot be explicitly recognized in this exemplary embodiment. It can be recognized especially from FIG. 18, which shows a front view XVIII from FIG. 15 of the tool 140, that the tool blades 143 and 144 are arranged in this exemplary embodiment with their respective longitudinal central planes 146 and 147 offset by an amount V in the circumferential direction in relation to the respective radial direction 148 and 149 and are connected with one another by an approximately S-shaped connection section 150 of equal width.

The bone screw 142 has in its screw head 141 two blade slots 151 and 152, which together form a linear, diametrically extending receiving slot for the tool blades 143 and 144. The width of the blade slots 151 and 152 is made only slightly larger than the width of the tool blades 143 and 144. The difference between the width of the blade slots 151, 152 and the width of the tool blades 143, 144 is at any rate smaller than the offset V of the tool blades 143, 144 in relation to their respective radial directions 148, 149. It is achieved by this embodiment that the tool blades 143 and 144 are elastically deformed together with the connection section 150 when attached and pushed into the blade slots 151, 152 and adapt themselves approximately to the linear course of the blade slots 151 and 152. The two blade slots 151, 152 are indicated by broken lines in FIG. 18, which show their linear course.

Figure 19:
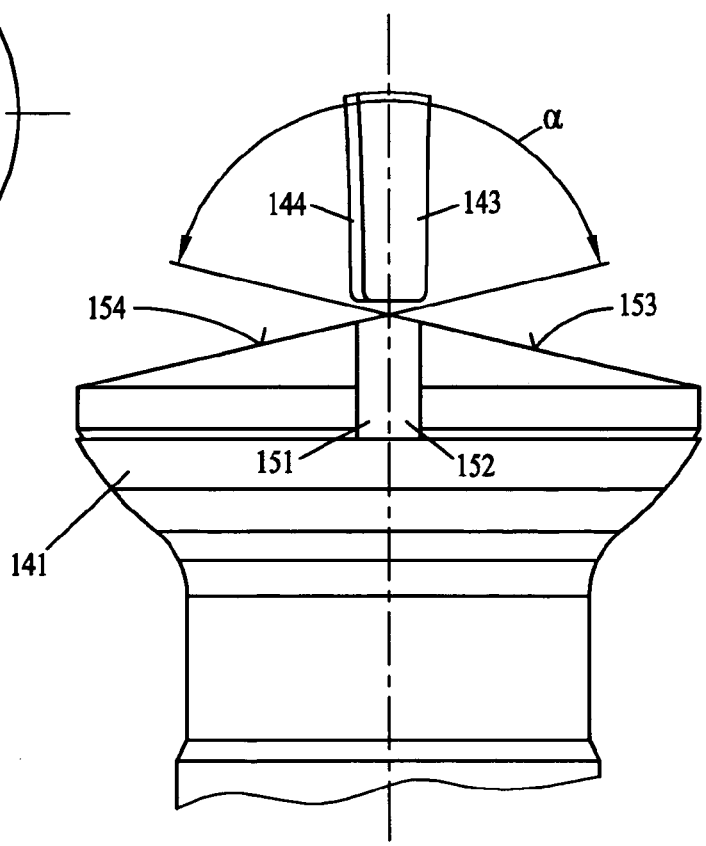
FIG. 19 is a side view XIX of the tool blade of the tool from FIG. 17 together with the screw head of the bone screw from FIG. 17.

FIG. 19 shows a side view XIX of the tool blades 143, 144 and of the screw head 141 with its two aligned blade slots 151 and 152. It can be recognized that the marginal edges of the tool blades 143 and 144 are rounded. The pushing in of the tool blades 143, 144 into the blade slots 151, 152 is considerably simplified by this embodiment. The upper marginal edges of the blade slots 151, 152 are also rounded, so that the tool blades 143, 144 can slide into the blade slots 151, 152 with elastic deformation of the tool blades 143, 144 via their rounded edges along the rounded edge of the blade slots 151, 152, without the risk of burring or another type of destruction of both the tool blades 143, 144 and of the blade slots 151, 152.

Furthermore, the tool blades 143 and 144 may be provided with separating slots 155, 156 in their radially outer end areas, as this is indicated by broken lines in FIG. 17. As a result, the radially outer end areas of the tool blades 143, 144 themselves form a clamping element 157 and 158, which are arranged offset in the circumferential direction in relation to the radially inner part of the corresponding tool blades 143, 144 corresponding to the views in FIGS. 18 and 19. The radially inner part of the tool blades 143, 144 may extend linearly here. A reliable clamping hold of the tool 140 at the bone screw 142 can be achieved with this embodiment as well.

Furthermore, it can be recognized from FIG. 19 that the axially outer front surfaces 153, 154 of the screw head 141 extend slopingly in relation to one another at a cone angle α, so that the surface of the screw head 141 has a conical shape. The cone angle α may likewise be between 145° and 160°, as in the exemplary embodiment according to FIG. 5. The insertion of the tool blades 143, 144 into the blade slots 151, 152 is considerably facilitated by this embodiment as well, because the tool blades 143, 144 can first be attached centrally "between" the blade slots 151, 152 with their connection section 150 shown in FIG. 17 and the tool blades 143, 144 will engage the blade slots 151, 152, while undergoing an elastic deformation, only when the tool blades 143, 144 are being pushed farther into the blade slots 151, 152.

The tool blades 143 and 144 may also be provided in the central area of their connection section 150 with an axially projecting pin, which can be caused to engage a corresponding central axial hole of the screw head 141 in a positive-locking manner, as this is shown as an example in connection with the exemplary embodiment according to FIGS. 8 and 9. This variant is not explicitly shown in the drawing. In the exemplary embodiments in which the clamping action is brought about between the tool blades and the blade slots, it is not absolutely necessary for the pin to act as a clamping element, but is usually used only to center the tool at the screw head. The diameter of the axial hole of the screw head is correspondingly made somewhat larger than the external diameter of the pin, namely, by about 0.1 mm to 0.3 mm.

Figure 20:
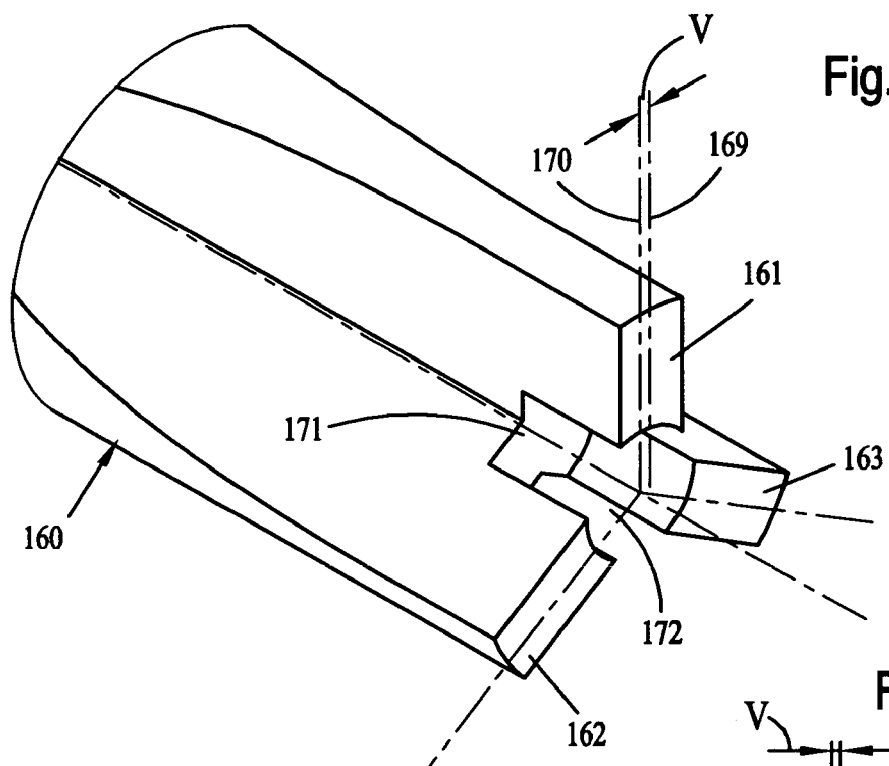
FIG. 20 is a perspective view of a tool with three tool blades and a central recess.
Figure 21:
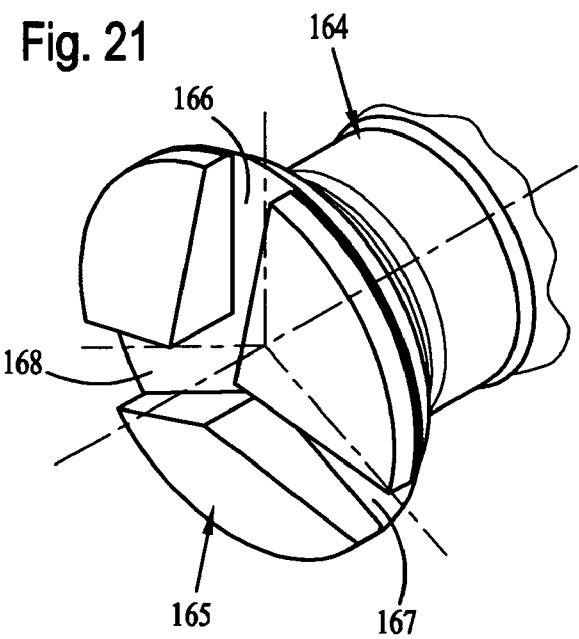
FIG. 21 is a perspective view of a screw head of a bone screw with three blade slots, fitting the tool from FIG. 20.

FIG. 20 shows another exemplary embodiment of a tool 160, which is provided with three tool blades 161, 162 and 163 arranged in a star-shaped pattern. The corresponding bone screw 164 is shown in FIG. 21 and has three blade slots 166, 167 and 168, which are likewise arranged in a star-shaped pattern in the screw head 165 and which engage the tool blades 161, 162 and 163 in the attached state.

To achieve the clamping hold of the screw head 165 at the tool 160 in this case as well, the tool blade 161 is arranged such that its radial central longitudinal axis 169 is offset by an amount V of about 0.025 mm to 0.25 mm in relation to a radial direction 170 extending in parallel to the tool blade 161. This offset V is also recognizable from FIG. 22, and this offset is shown for illustration as a considerably greater offset than it is in reality in order to graphically illustrate the embodiment according to the present invention.

Figure 18:
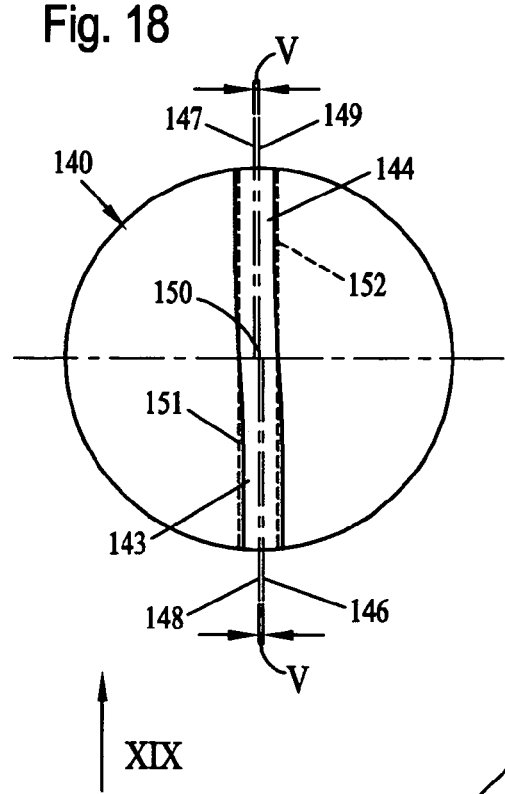
FIG. 18 is a top view XVIII of the tool from FIG. 17.

To make it now possible to engage this tool blade 161 arranged with an offset with the corresponding blade slot 166, both the marginal edges of the tool blades 161, 162, 163 and the limiting edges of the blade slots 166, 167 and 168 are rounded or are provided with a bevel, similarly to how it was explained in connection with FIG. 19 (not explicitly shown in the drawings in connection with FIGS. 18 and 19). To achieve a greater elastic flexibility of the offset tool blade 161, a central axial hole 172, which may have a depth of 0.5 mm to 2.5 mm, is provided in the area of the shank core 171 of the tool 160 in the exemplary embodiment according to FIG. 18, the depth of this axial hole being likewise dependent here on the overall dimensions of the tool 160 and being the greater the larger the tool 160 is. The tool blades 161, 162 and 163 are separated by this axial hole 172 in the area of the shank core 171, so that each of the tool blades 161, 162, 163 is elastically deformable in the circumferential direction. The amount of the elastic flexibility of the tool blades 161, 162, 163 can be determined by selecting the axial depth of the axial hole 172, so that despite their flexibility, these do not have sufficient rigidity to undergo a permanent deformation during the tightening of a bone screws.

Instead of this axial hole 172, it is also possible to provide cross slots, especially in tools with an even number of tool blades, as this is described as an example in connection with the exemplary embodiment according to FIGS. 2 through 4.

Figure 20A:
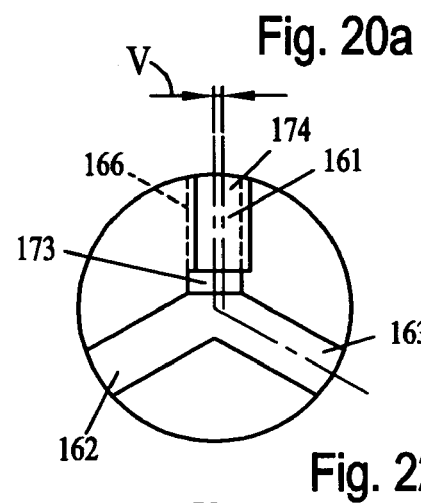
FIG. 20a is the top view of an alternative embodiment of the tool from FIG. 20.
Figure 22:
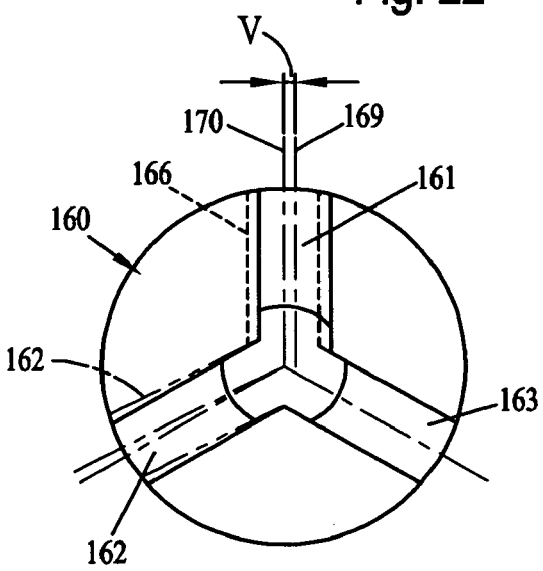
FIG. 22 is a top view of the tool from FIG. 20.

Provisions may also be made here for, e.g., the tool blades 161 and 162 to be in connection with one another in the area of the shank core and for only the tool blade 161 to be separated by a separating slot 173 from the shank core 171. Thus, the tool blade forms a clamping element 174 itself due to its offset in the circumferential direction (FIG. 22). This embodiment is shown as an example in a top view in FIG. 20a.

In other words, the position of the tool blade 161 adapts itself to the position of the associated blade slot 166 during attachment to the screw head 165. The blade slot 166 is indicated by broken lines in FIG. 22. It is easy to imagine that during a slight offset V of the tool blade 161, as was referred to above, the tool blade moves from its position indicated by solid lines in FIG. 22 into the position of the blade slot 166 indicated by broken lines while undergoing elastic deformation. A clamping hold action, by which the bone screw 164 is held securely but detachably at the tool 160, is achieved now as a result between all tool blades 161, 162, 163 and blade slots 166, 167, 168.

Furthermore, it can be recognized from FIG. 22 that instead of the offset V or in addition thereto, one or more tool blades may be arranged offset by a small angle of about 0.5° to 1° in relation to the radial direction extending symmetrically between two adjacent tool blades. Such an offset is indicated by phantom lines for the tool blade 162 in FIG. 22. Clamping action can also be achieved by this embodiment between the tool blades and the blade slots. The tool blades may also have a slightly bent, radial course, which is not explicitly shown in the drawings.

Figure 23:
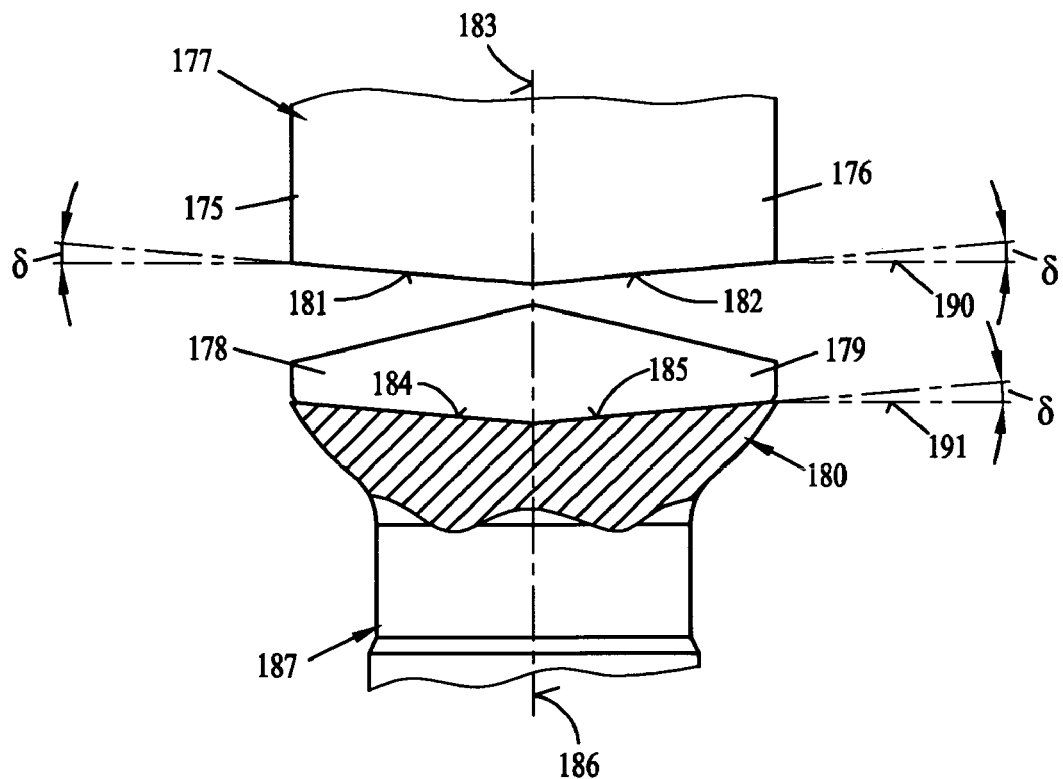
FIG. 23 is a partial section of a tool with beveled tool blades and of a screw head with beveled blade slots.
Figure 24:
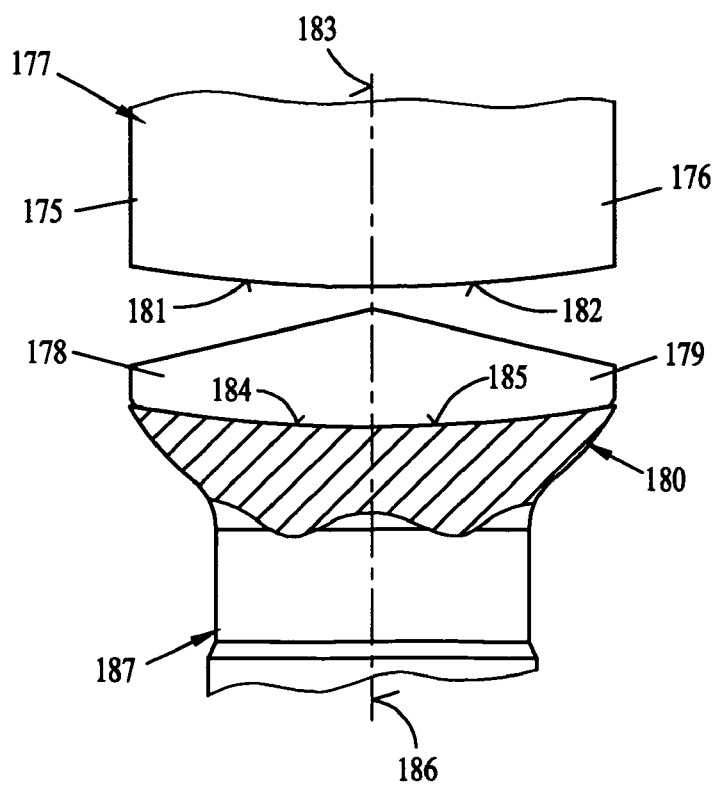
FIG. 24 is a partial section of a tool with tool blades extending in an arc-shaped pattern and of a screw head with blade slots extending in an arc-shaped pattern.

FIGS. 23 and 24 show two exemplary embodiments, in which two tool blades 175, 176 are provided at the tool 177 and two blade slots 178, 179 on the screw head 180, the shape and the bearing position of the tool blades and blade slots corresponding essentially to the design of the exemplary embodiment shown in FIG. 17.

In the exemplary embodiment according to FIG. 23, the axially outer front surfaces 181 and 182 of the tool blades 175, 176 extend at a pitch angle δ to a transverse plane 190 extending at right angles to the central longitudinal axis 183 of the tool 177. This pitch angle δ may assume values between 3° and 10°. The two bases 184 and 185 of the associated blade slots 178, 179 also extend at the same pitch angle δ in relation to a transverse plane 191 extending at right angles to the central longitudinal axis 186 of the bone screw 187 corresponding to this embodiment of the tool blades 175, 176. "Angle errors" occurring during the manual screwing in of a bone screw are compensated by this embodiment. An angle error is defined here as a non-coaxial orientation of the tool 177 in relation to the central longitudinal axis 186 of the bone screw 187 to be screwed in. Certain "wobblings" of the screwdriver, which are effectively compensated by the special shape of the tool blades 175, 176, on the one hand, and of the blade slots 178, 179, on the other hand, always occur during the manual actuation of a screwdriver (by hand).

As an alternative to the embodiment according to FIG. 23, provisions may also be made for the axially outer front surfaces 181 and 182 of the tool blades 175, 176 to have an arc-shaped course, as this is shown in FIG. 24. The bases 184, 185 of the blade slots 178, 179 of the screw head 187 are also designed corresponding to this course. "Angle errors" occurring during the screwing in of a bone screw are also compensated by this embodiment.

It shall be mentioned here once again that the special embodiments described in connection with the individual exemplary embodiments can be embodied both alone and in any combination with one another. It is common to all features and combinations of features that the tool is held securely clampingly and detachably at a bone screw and no other device is needed to bring about a reliable holding of the tool at the screw head (or vice versa). In particular, clamping elements, which may also be formed by the tool blades themselves, are provided at the tool blades.

While specific embodiments of the invention have been shown and described in detail to illustrate the application of the principles of the invention, it will be understood that the invention may be embodied otherwise without departing from such principles.

What is claimed is:

1. A system comprising:
a screwdriver having a tool shank and a tool element with at least two axially and radially extending tool blades, each tool blade having at least one elastic clamping section, said elastic clamping section being moveable from a first position to a second position, said tool element having a central shank core, said tool blades being formed by uniform cutouts of a rotationally symmetrical blade shank, said cutouts having a triangular cross section, said tool blades being connected with one another in one piece via said central shank core, one tool blade being connected with another tool blade in one piece via said central shank core, each tool blade having a front surface extending along a cross section of said tool shank in a direction substantially perpendicular to a longitudinal axis of said tool shank, said tool blades having separating slots, each tool blade being elastic in a circumferential direction via said separating slots; and
a bone screw with groove-like blade slots, each tool blade engaging each groove-like slot such that said bone screw moves said clamping section from said first position to said second position when said bone screw is connected to said tool element, whereby said clamping section clampingly engages said bone screw in said second position.

2. A system in accordance with claim 1, wherein said blade slots of the bone screw open in a central, cylindrical axial hole of the bone screw, and that the clamping sections of the tool blades are formed from elastically flexible clamping elements which protrude each axially from the front surfaces of said tool blades, and whose clamping surfaces are located on an external diameter that is adapted to the diameter of the axial hole to bring about a clamped connection.

3. A system in accordance with claim 2, wherein inner limiting surfaces of ring sectors, which are located between the individual blade slots and are formed by said blade slots, form partial surfaces of a cylinder having a diameter greater than the diameter of the axial hole by a factor of 0.05 to 0.2.

4. A system in accordance with claim 3, wherein axially outer front surfaces of the ring sectors form partial surfaces of the envelope of a cone, whose cone angle is between 145° and 160°.

5. A system in accordance with claim 1, wherein axial center planes of said blade slots intersect each other in the axis of the screw and that the width of said blade slots corresponds to one fifth of the diameter of the screw head.

6. A system in accordance with claim 2, wherein the diameter of the central axial hole corresponds to at least one third of the diameter of the screw head and that the depth of the axial hole corresponds to at least one tenth to one eighth of the diameter of the screw head.

7. A system in accordance with claim 1, wherein each of said clamping sections comprises an axially protruding sector of a circular ring, which is concentric with the axis of the blade shank, said sectors being formed by cutouts which define said tool blades.

8. A system in accordance with claim 1, wherein said clamping sections comprise sectors of a circular ring, said sectors being located on a front surface of a tool blade and formed by radially extending grooves.

9. A system in accordance with claim 1, wherein:
said clamping sections comprise the circular sectors of a central cylindrical pin, said sectors being formed by at least two diametrically extending grooves, which intersect each other and are open on the front side and radially;
said grooves penetrate the shank core and have an axial depth that is at least twice the axial height of said clamping elements; and
said grooves are each respectively located in the planes of symmetry of two diametrically opposed cutouts.

10. A system in accordance with claim 9, wherein:
there are fewer circular sectors than tool blades, wherein two said diametrically opposite tool blades of six tool blades have separate circular sectors on front surfaces thereof;
respective front surfaces of two said tool blades located in between in the circumferential direction, together carry a circular sector.

11. A system in accordance with claim 9, wherein said clamping sections have a circumferential surface tapering conically toward a plane of the front surfaces of said tool blades at a angle ($\beta$) of 2° to 6° and a beveled or rounded marginal edge.

12. A system in accordance with claim 1, wherein at least one of said tool blades has, at least in an outer end area engaging said blade slots, a course deviating from the course of said blade slots such that said tool blades can be caused to clampingly engage surfaces defining said blade slots, and said tool blades are designed as dimensionally stable and elastic tool blades.

13. A system in accordance with claim 12, wherein said deviation of the course of the tool blade from the associated blade slot of the bone screw is in the range between 0.025 mm and 0.25 mm.

14. A system in accordance with claim 1, wherein the tool has a central shank core, which is provided with one or more axial recesses, which separate said tool blades at least in their end areas that can be caused to engage said blade slots.

15. A system in accordance with claim 14, wherein the recess is formed from a blind hole, which is prepared on the front side in the shank core and has an axial depth of 0.5 mm to 2.5 mm starting from the axially outer front surfaces of said tool blades.

16. A system in accordance with claim 14, wherein the recesses are formed from said axially extending grooves, which have an axial depth of 0.5 mm to 2.5 mm starting from the axially outer front surfaces of said tool blades.

17. A system in accordance with claim 1, wherein a centering pin, which axially protrudes over said tool blades and whose diameter is greater than the shank core, is provided in the area of the shank core, and that the centering pin engages a central axial hole of the bone screw in the state in which the tool is attached to the bone screw.

18. A system in accordance with claim 1, wherein axially outer front surfaces of said tool blades extend obliquely outwardly, linearly set back or in an arch-shaped pattern starting from the shank core at a cone angle δ of 3° to 10° in relation to a plane extending at right angles to the central longitudinal axis of the shank core, and that the bases of the associated blade slots of the bone screw have the same course.

19. A system comprising:

a screwdriver having a tool shank and a tool element with a first axially and radially extending tool blade and a second axially and radially extending tool blade, said first tool blade having a first retaining element, said second tool blade having a second retaining element, said tool element having a central core shank, said first axially and radially extending tool blade and said second axially and radially extending tool blade being integrally connected to said central core shank, each tool blade having a front surface extending along a cross sectional length of said tool shank in a direction substantially perpendicular to a longitudinal axis of said tool shank; and a bone screw having an outer surface defining a first groove-like blade slot and a second groove-like blade slot, said bone screw having an inner surface defining a retaining element insertion gap, said first tool blade engaging said first blade slot, said second tool blade engaging said second blade slot, said first retaining element and said second retaining element being flexible to generate a snap in retaining function as said first retaining element and said second retaining element is moved into said retaining element insertion gap, whereby said bone screw is connected to said screwdriver.

20. A system in accordance with claim 19, wherein:

said retaining elements comprise the circular sectors of a central cylindrical pin, said sectors being formed by at least two diametrically extending grooves, which intersect each other and are open on the front side and radially;

said grooves penetrate the shank core and have an axial depth that is at least twice the axial height of said clamping elements; and said grooves are each respectively located in the planes of symmetry of two diametrically opposed cutouts.

* * * * *